United States Patent

Shoher et al.

[11] Patent Number: 5,234,343
[45] Date of Patent: Aug. 10, 1993

[54] MOLDABLE DENTAL MATERIAL AND METHOD

[76] Inventors: Itzhak Shoher, 50 Shlomo Hamelechst, Tel-Aviv, Israel, 64386; Aharon E. Whiteman, J.L. Peretz St 13, Petach-Tikvah, Israel, 49206

[21] Appl. No.: 887,245

[22] Filed: May 19, 1992

Related U.S. Application Data

[63] Continuation of Ser. No. 801,028, Dec. 2, 1991, abandoned.

[51] Int. Cl.⁵ .................................................. A61C 5/00
[52] U.S. Cl. ................................. 433/215; 433/218; 433/223; 433/228.1; 433/213; 428/212; 29/160.6; 75/228
[58] Field of Search ............... 423/213, 214, 215, 218, 423/223, 228.1; 29/160.6; 428/212; 75/228

[56] References Cited

U.S. PATENT DOCUMENTS

| | | | |
|---|---|---|---|
| 3,502,466 | 3/1970 | Vickery | 75/208 |
| 4,355,980 | 10/1982 | Dwight | 433/228.1 |
| 4,426,404 | 1/1984 | Shoher et al. | 433/223 |
| 4,468,251 | 8/1984 | Hausselt et al. | 433/218 |
| 4,554,218 | 11/1985 | Gardner et al. | 428/567 |
| 4,602,953 | 7/1986 | Wiech, Jr. | 75/228 |
| 4,676,751 | 6/1987 | Shoher et al. | 433/218 |
| 4,689,197 | 8/1987 | Groll et al. | 418/23 |
| 4,698,021 | 10/1987 | Shoher et al. | 433/218 |
| 4,742,861 | 5/1988 | Shoher et al. | 164/80 |
| 4,814,008 | 3/1989 | Shoher et al. | 75/252 |
| 4,846,718 | 7/1989 | Rieger | 433/218 |
| 4,940,637 | 7/1990 | Shoher et al. | 433/218 |
| 4,978,298 | 12/1990 | Eliasz | 433/213 |
| 4,990,394 | 2/1991 | Shoher et al. | 433/228.1 |
| 4,997,699 | 3/1991 | Shoher et al. | 428/212 |
| 5,094,689 | 3/1992 | Stuemke et al. | 106/35 |

FOREIGN PATENT DOCUMENTS 0052922 2/1982 European Pat. Off. .
1271157 4/1972 United Kingdom .

*Primary Examiner*—John J. Wilson
*Attorney, Agent, or Firm*—E. Lieberstein

[57] ABSTRACT

A moldable dental composition for use in forming or repairing dental restorations composed of a mixture of high- and low-fusing temperature metal particles and a wax in a concentration of between thirty to eighty percent by volume of the mixture. The average particle size of the metal particles are above one micron, with the high-fusing temperature metal particles at least twice the size of the low-fusing metal particles. The composition is heat treated at a temperature to melt the low-fusing temperature metal particles and to eliminate the wax, leaving a porous metal structure with a void volume above thirty percent. The voids are filled using a filler material of metal or ceramic.

20 Claims, 1 Drawing Sheet

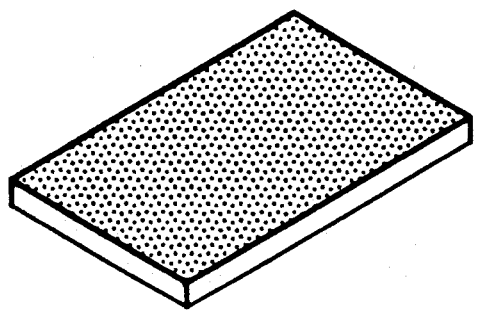
Fig. 1
Fig. 1A
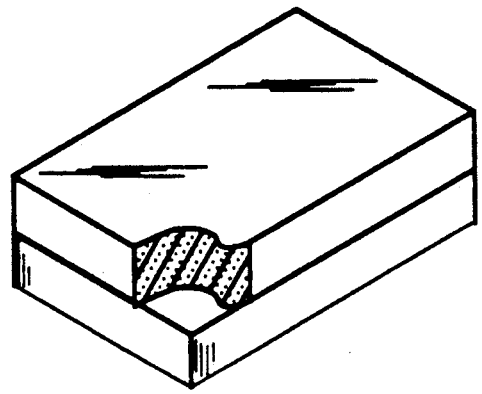
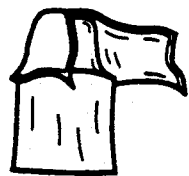
Fig. 2
Fig. 3
Fig. 4

MOLDABLE DENTAL MATERIAL AND METHOD

This application is a continuation of application Ser. No. 801,028, filed Dec. 2, 1991 now abandoned.

FIELD OF THE INVENTION

This invention relates to a moldable dental material composition and to a method for forming and/or repairing ceramic-to-metal dental restorations using such material.

BACKGROUND OF THE INVENTION

A metal coping is used in dentistry in the construction of a dental crown and bridge. The metal coping functions as the understructure of the crown and is usually covered, for reasons of aesthetics, with a fired-on coating of ceramic porcelain composition or an acrylic. The metal coping supports the coating and provides the required structural strength and rigidity for the restored tooth to resist the forces of mastication.

The customary practice is to cast the metal coping from an investment of a wax or plastic pattern of the tooth to be restored. The restoration formed using this procedure is conventionally referred to as a cast metal restoration. A metal coping has recently been developed for constructing a porcelain to metal crown which does not require waxing, investing or casting. The coping is formed from a prefabricated metal foil arranged in a prefolded configuration, with a plurality of foldable sections as described in more detail, in Reissue Pat. No. 33,099, which issued to Applicant on Oct. 24, 1989. An alternative method of forming a dental coping from a metal foil is taught by Applicant in U.S. Pat. No. 4,861,267, which issued on Aug. 29, 1989. In each instance, the starting material for forming the coping is a solid metal foil formed from a lamination of solid metal layers, each of a precious metal. The preferred arrangement is a lamination of layers of palladium disposed between gold or gold alloy layers, as taught by Applicant in another U.S. Pat. No. 4,698,021 issued on Oct. 6, 1987. To form a coping from a preformed metal foil, the foil must be fitted and adapted to the die of the tooth to be restored and then swedged to conform to the die. The adaptation procedure is intended to be practiced by a dental technician in the dental laboratory and requires training and skill to achieve accuracy in getting a good fit at the margin.

SUMMARY OF THE INVENTION

A dental composition has been discovered which can be molded with minimal skill for forming a metal coping directly on a refractory die, or for repairing a dental restoration. This can be readily practiced either at the dental laboratory or by the dentist in the dental office.

The composition of the present invention comprises: a uniform mixture of high-fusing temperature metal particles having an average particle size between 4 to 80 microns, and a melting temperature above a preselected heat treatment temperature; low-fusing temperature metal particles having an average particle size between 2 to 25 microns, and a melting temperature equal to or below said preselected heat treatment temperature; and a wax, with the wax in a concentration of at least about thirty percent by volume, such that upon heat treatment at said heat treatment temperature, a porous metal structure is formed having a capillary network of voids and a void volume of between thirty to eighty percent.

The method of the present invention for forming a dental metal restoration comprises the steps of:

applying a first mixture composed of particles of a high-fusing temperature metal, particles of a low-fusing temperature metal, and a wax representing at least thirty percent by volume of the mixture to a die or model of the tooth to be restored;

heat treating the mixture at a temperature below the melting temperature of the high-fusing temperature metal particles, and at or above the melting temperature of the low-fusing temperature metal particles, to form a porous structure composed of said metals with a void volume of between thirty percent to eighty percent;

shaping the heat-treated porous structure, in situ, into the desired configuration for the dental metal restoration;

applying a second mixture composed of particles of filler material in a wax composition, with the wax representing at least about thirty percent by volume of the mixture over said shaped structure; and heat treating the structure at a temperature below the melting temperature of the high-fusing metal, but high enough to melt said filler material into said porous structure for densifying said structure into a solid.

BRIEF DESCRIPTION OF THE DRAWINGS

Additional advantages of the present invention will become apparent from the following detailed description of the invention when read in conjunction with the accompanying drawings of which:

FIG. 1 is a perspective view of a compacted strip formed from the dental composition of the present invention;

FIG. 1A is a view similar to FIG. 1 of a compacted strip formed of two layers;

FIG. 2 is a transparency in perspective of the waxed coping hand-molded over the die of a prepared tooth, with the coping shown opened to illustrate thickness;

FIG. 3 is a perspective of the metal coping formed on the die of FIG. 2 after heat treatment; and FIG. 4 is an illustration in perspective of the finished dental coping of FIG. 3 upon removal from the die.

DETAIL DESCRIPTION OF A PREFERRED EMBODIMENT OF THE INVENTION

The dental material of the present invention is a moldable composition formed from a mixture of metal particles of high- and low-fusing temperature metals and a wax. The concentration of the wax must be at least thirty percent by volume of the mixture, and up to eighty percent. The wax composition permits the material to be heat treated for forming a porous sponge-like structure having multiple voids uniformly distributed throughout the structure, for forming a capillary network of voids and a void volume of at least thirty percent. The high content of wax creates an accurate network of capillary passages between voids upon heat treatment. The uniformity and homogeneity in the network of voids has been found to be essential for making a dental restoration in accordance with the present invention. The voids formed in the heat-treated material on a volume basis ("void volume") may range between forty to eighty percent by volume, and preferably between forty and sixty-five percent by volume. Upon heat treatment the wax escapes, leaving a porous metal structure with essentially little or no shrinkage.

In accordance with the present invention, a filler material is melted into the voids of the heat-treated porous structure to densify the structure for forming the final dental restoration. The porous metal structure is first shaped into a desired configuration for forming a dental restoration before the filler material is added. The filler material may be any suitable ceramic or metal composition, preferably a precious metal composition. It is a preferred embodiment of the present invention to form a matrix of particles of filler material, which are mixed with a wax component in a concentration similar to the wax concentration used to form the porous structure, from the mixture of high- and low-fusing temperature metal particles. A minimum wax concentration of at least about thirty percent by volume is preferred, and up to seventy-five percent by volume. The filler particles may be an alloy of at least fifty percent by weight of gold with other metals such as silver, copper, zinc, aluminum, magnesium, gallium, indium, or any of the platinum group metals and/or elements from the third or fourth groups of elements of the periodic table of elements to form a melting gradient during melting of the filler material, such that the filler particles melt in a preferred sequence. A maximum of up to seven percent (7%) silver and a maximum of up to ten percent (10%) of other elements is preferred. Fluxes may also be included in the filler material.

The wax composition itself is not critical to the invention, and any natural wax, mineral wax, or organic wax composition may be used. The preferred wax is relatively soft and tacky, and should melt relatively cleanly without leaving a significant residue. The melting temperature of the wax must be below the melting temperature of the low-fusing temperature metal particles, and below the melting temperature for the filler material. Moreover, the high- and low-fusing temperature metal particles should combine readily with the wax at room temperature to form a mixture with a uniform distribution of metal particles in the wax. Alternatively, the wax can be heated and the particles added and mixed, to form a uniform distribution of metal particles.

The high-fusing temperature metal component of the base mixture of high- and low-fusing temperature metal particles may be a single metal or metal alloy, preferably of precious metals such as platinum and palladium, in any desired proportion relative to each other from zero to one hundred percent, with or without other constituents such as Au*. Gold may be added to the high-fusing temperature metal component to increase the affinity of the high-fusing temperature metal component to the low-fusing temperature metal component. The particles of low-fusing temperature metal are composed preferably of gold or a gold alloy, with gold as the major constituent. The preference for gold as the major constituent of the low-fusing component is based on its known characteristics of workability, biocompatibility, non-oxidizing properties, and color. The particles of high- and low-fusing temperature metal should be selected with the high-fusing temperature component having an average size of at least 4 microns and up to a maximum size of 80 microns. The size of the particles of high-fusing temperature metal should be between two and ten times larger than the particle size of the low-fusing metal particles, and preferably between five and ten times larger in size. The low-fusing particles must have an average size equal to or above two microns and a preferred size range of between 2 to 25 microns. The volume relationship of the metals in the mixture should be in a range of from about ten to sixty percent of the low-fusing component relative to the high-fusing component, and preferably from 25 to 40 percent. The composition of the selected metal particles for the high- and low-fusing components will determine the optimum volume ratio. The weight ratio will vary with the specific gravity of the selected materials as evidenced by the examples at the end of the specification.

*Ag, Cu, Mg, Al, Zn, and other metals of the platinum group of elements of the third and fourth group of elements. The total weight percent of the elements other than gold, silver, and platinum group metals should not exceed ten percent.

The size of the metal particles, their ratio, and the concentration of wax in the base mixture of high- and low-fusing temperature metal particles will control the void volume of the porous structure after heat treatment, as well as the uniformity of the capillary network formed between the voids which, in turn, controls the absorption and accommodation of the filler material in the porous structure. The heat treatment must eliminate the wax, preferably without leaving a residue, and cause the low-fusing particles to melt to form a porous metal structure with a forty to eighty percent void volume and a uniformly distributed void matrix.

In accordance with the preferred method of the invention, the base mixture of wax and high- and low-fusing temperature metal particles are compressed into a compacted strip (10), as shown in FIG. 1 in the form of a rectangular sheet, although any geometrical shape may be formed, including a cylindrical rodlike shape. The sheet thickness may lie between 50 and 1000 microns, depending upon the specific application, with a thickness between 150 to 500 microns preferred for forming a dental coping. The filler material and wax may, likewise, be compacted into a strip or other geometry, for ease of application to the porous structure formed from the base mixture.

Different metal-wax mixtures may be used to form laminated layers for special applications where, for example, it is preferable to have a variation in the void volume characteristic of the porous structure formed after heat treatment. For example, a compacted strip (10) composed of two layers, as shown in FIG. 1A, may be formed with one layer having twice as much wax as the other. This will result in a porous structure which has roughly twice the void volume in its exterior or interior, depending on whether the interior or exterior has the higher wax concentration. Moreover, the layer thickness may be varied and/or different metal alloy compositions may be used to form each layer. The number of layers in the strip (10), their composition, arrangement, and thickness can be used to predetermine the properties of the porous structure.

The filler material-wax composition may also be formed into a compacted strip (not shown) or may be laminated over the strip (10) of base material, similar to FIG. 1A. If they are preclad, it is still essential that the heat treatment be at a first temperature which will form a porous structure without melting the filler material. However, the wax component in each layer may be volatilized or be otherwise eliminated through melting. Thereafter, the heat treatment temperature may be raised to melt the filler material into the voids of the porous structure. Although the filler material should not melt or disturb the sintering process of the base material, components of the filler material, such as fluxes, binders, etc., may indeed melt into the porous structure during this first heat treatment.

When the porous sponge-like structure is formed from an independent strip (10) of base material, the filler material may have a sintering temperature of more or less than that of the sintering temperature of the low-fusing temperature metal particles in the base material.

To form coping from a strip (10) of base material, the strip (10) is preferably cut into pieces or sections which are applied to the surface of a die. The pieces are hand-molded, using pressure, with or without the use of an adhesive. The adhesive may be composed of a wax with a solvent and may include other components, such as other adhesive agents, fluxes, etc. Hand-molding is done with the aid of a spatula or other hand instrument. The carving of the base metal-wax material into a preferred shape may be done on a model and then removed, or supported in any other fashion, for heat treatment. The heat treatment may be done in a furnace or under a flame. The usual heat treatment temperature range for the base material is between 800° C. and 1200° C. The heat treatment of the filler material may also be done in a furnace or using a flame.

The pieces of wax-strip (10) are easily shaped or carved into any desired geometry, as shown in FIG. 2, with little effort and require no expertise. The wax coping can be up to 1000 microns in thickness. The heat treatment may be carried out directly on the die, with the wax absorbed into the die, leaving a sponge-like structure, as shown in FIG. 3. As the temperature is raised to the sintering temperature, the wax burns out and the sinterization process forms the spongy structure. Filler material is then added to the porous structure and heat treated to form a dense solid coping, as shown in FIG. 4.

The following are examples illustrating the volume-weight relationship between the low- and high-fusing temperature metals in the base metal composition for three different high-fusing metal compositions:

EXAMPLE 1

The relationship between low-fusing and high-fusing metals in the metal composition that reflects differences in their specific gravity.

| Alloy (specific gravity gr/cm³)* | | Volume % | | Weight % | |
| --- | --- | --- | --- | --- | --- |
| Low Fusing | High Fusing | Low Fus. | High Fus. | Low Fus. | High Fus. |
| (A) | | | | | |
| Au (19.3)* melting temperature 1063° C. | Pt (21.43)* 1773° C. | 30 | 70 | 27.8 | 72.2 |
| (B) | | | | | |
| Au (19.3)* melting temperature 1063° C. | Au 87% Pt 7% Pd 8% (17.8)* 1187° C. | 30 | 70 | 32.1 | 87.9 |
| (C) | | | | | |
| Au (19.3)* melting temperature 1063° C. | Pd (12.0)* 1554° C. | 30 | 70 | 40.8 | 59.2 |

EXAMPLE 2

Examples of weight relations in composition of 50% wax and 50% metals (= low-fusing + high-fusing) by volume.

| Specific Gravity (gr/cm³) | | Volume % | | Weight % | |
| --- | --- | --- | --- | --- | --- |
| Metal Composition | Wax | Metals | Wax | Metals | Wax |
| (A) | | | | | |
| (20.8) | (0.9) | 50 | 50 | 85.85 | 4.15 |
| (B) | | | | | |
| (18.0) | (0.9) | 50 | 50 | 95.24 | 4.75 |
| (C) | | | | | |
| (14.2) | (0.9) | 50 | 50 | 94.04 | 5.96 |

EXAMPLE 3

Volume and weight relations of different metal composition (A) - wax mixtures.

| Volume % | | Weight % | |
| --- | --- | --- | --- |
| Metal | Wax | Metal | Wax |
| 25 | 75 | 88.50 | 11.50 |
| 50 | 50 | 95.24 | 4.76 |
| 75 | 25 | 98.58 | 1.43 |

It should be understood that the dental material of the present invention can be used for repair work or to join two restorations at the interproximal. The repair work can be of a preformed metal restoration or of a cast metal restoration.

What is claimed is:

1. A moldable dental composition comprising: a uniform mixture of high-fusing temperature metal particles having an average particle size above one micron, and a melting temperature above a preselected heat treatment temperature; low-fusing temperature metal particles having a melting temperature equal to or below said preselected heat treatment temperature; and a wax binder having a wax concentration of between about thirty percent (30%) to eighty percent by volume of the mixture, such that upon heat treatment at said heat treatment temperature, a porous metal structure is formed having a capillary network of interconnecting voids and a void volume of between thirty to eighty percent.

2. A moldable dental composition, as defined in claim 1, wherein said high- and low-fusing temperature metal particles are precious metals.

3. A moldable dental composition, as defined in claim 1, wherein said highfusing temperature metal particles have an average particles size between 4 to 80 microns, and wherein said low-fusing temperature metal particles have an average particles size between 2 to 25 microns.

4. A moldable dental composition, as defined in claim 3, wherein the low-fusing temperature metal component is between 10 to 60 percent by volume of said composition.

5. A moldable dental composition, as defined in claim 4, wherein the void volume of said porous structure is between 35 to 65 percent.

6. A moldable dental composition, as define in claim further comprising a second composition for densifying the porous metal structure formed upon heat treatment of said uniform mixture of high- and low-fusing metal particles, wherein said second composition comprises a mixture of particles of a filler material, having a melting temperature below the melting temperature of said high-fusing metal component, and wax, with said wax in a concentration of at least about thirty percent by volume of said second composition.

7. A moldable dental composition, as defined in claim 6, wherein said second composition is gold or an alloy of at least fifty percent by weight of gold and a metal selected from the group consisting of other metals such as silver, copper, zinc, aluminum, magnesium, gallium, indium, or any of the platinum group metals and/or elements from the third or fourth groups of elements of the periodic table of elements.

8. A moldable dental composition, as defined in claim 7, further comprising a flux.

9. A moldable dental composition, as defined in claim 6, wherein said second composition is in the form of a compacted strip.

10. A moldable dental composition, as defined in claim 4, wherein said mixture of high- and low-fusing temperature metals and wax is in the form of a compacted strip having a thickness of between 50 to 1000 microns.

11. A moldable dental composition, as defined in claim 10, wherein said thickness is between 150 to 500 microns for forming a dental metal coping from said strip.

12. A moldable dental composition, as defined in claim 10, wherein said mixture is formed into a strip having more than one layer, with each layer having a different wax concentration.

13. A moldable dental composition, as defined in claim 3, wherein said average high-fusing metal particles should be at least twice the size of said average low-fusing metal particle.

14. A method for forming a dental metal restoration, comprising the steps of:

applying a first mixture comprising particles of a high-fusing temperature metal, particles of a low-fusing temperature metal, and a wax representing at least thirty percent by volume of the mixture to a die or model of the tooth to be restored;

shaping the mixture upon said die into the desired configuration for the dental metal restoration;

heat treating the shaped mixture at a temperature below the melting temperature of the high-fusing temperature metal particles to form a porous structure composed of said metals with a void volume of between thirty percent to eighty percent;

applying a second mixture comprising particles of filler material in a wax composition, with the wax representing at least about thirty percent by volume of the mixture over said porous structure; and heat treating the porous structure at a temperature below the melting temperature of the high-fusing metal, but high enough to melt said filler material into said porous structure for densifying said structure into a solid.

15. A method for forming, repairing, or restoring a dental metal restoration, comprising the steps of:

applying a first mixture comprising particles of a high-fusing temperature metal, particles of a low-fusing temperature metal, and a wax representing at least thirty percent by volume of the mixture to a die or model of the tooth to be restored;

shaping the mixture upon said die into a desired configuration;

heat treating the shaped mixture at a temperature below the melting temperature of the high-fusing temperature metal particles, and between 800° C. and 1200° C. to form a porous structure composed of said metals with a void volume of between thirty percent to eighty percent; and filling the porous structure with a filler material for densifying said porous structure into a solid structure.

16. A method, as defined in claim 15, further comprising compressing said first mixture into a desired compacted geometry.

17. A method, as defined in claim 16, wherein said filler material comprises gold or a gold alloy of at least 50 percent by weight of gold and a metal comprising palladium and platinum.

18. A method, as defined in claim 17, wherein said metal alloy further comprises a metal selected from the group consisting of silver, copper, zinc, aluminum, magnesium, gallium, indium, or any of the elements from the third or fourth group of elements of the periodic table.

19. A method, as defined in claim 17, wherein said filler material is a mixture comprising particles of said gold or gold alloy and wax.

20. A method, as defined in claim 19, wherein said filler metal is heat-treated to melt at a temperature below the melting temperature of said high-fusing metal component.

* * * * *